United States Patent [19]

Adams et al.

[11] Patent Number: 5,395,383
[45] Date of Patent: Mar. 7, 1995

[54] ADHESION BARRIER APPLICATOR

[75] Inventors: Ronald D. Adams, Wyoming, Ohio; Richard M. O'Grady, Southington; Robert L. Marvin, Jr., New Britain, both of Conn.; Mary B. Youtsler, Cincinnati, Ohio; Michael T. Brown, Hillsborough, N.J.

[73] Assignee: Ethicon, Inc., Somerville, N.J.

[21] Appl. No.: 187,376

[22] Filed: Jan. 27, 1994

Related U.S. Application Data

[63] Continuation of Ser. No. 779,432, Oct. 18, 1991, abandoned.

[51] Int. Cl.6 .............................................. A61B 17/00
[52] U.S. Cl. ..................... 606/151; 604/14; 606/198
[58] Field of Search ............... 604/105, 106, 107, 127, 604/158, 264, 207, 14, 15.16, 271; 606/127, 198, 199, 200, 205, 151, 213, 214

[56] References Cited

U.S. PATENT DOCUMENTS

| | | | |
|---|---|---|---|
| 1,878,671 | 9/1932 | Cantor | 606/191 |
| 2,067,031 | 1/1937 | Wappler | 128/5 |
| 3,857,395 | 12/1974 | Johnson et al. | 606/198 |
| 4,411,655 | 10/1983 | Schreck | 604/104 X |
| 4,590,938 | 5/1986 | Segura et al. | 606/127 |
| 4,654,028 | 3/1987 | Suma | 604/106 |
| 4,655,219 | 4/1987 | Petruzzi | 606/206 |
| 4,705,041 | 11/1987 | Kim | 606/108 |
| 4,744,363 | 5/1988 | Hasson | 606/1 |
| 4,909,789 | 3/1990 | Taguchi et al. | 604/107 |
| 4,935,006 | 6/1990 | Hasson | 604/268 X |
| 5,057,114 | 10/1991 | Wittich et al. | 606/127 |
| 5,113,846 | 5/1992 | Hiltebrandt et al. | 604/105 X |

FOREIGN PATENT DOCUMENTS 160870 11/1985 European Pat. Off. .
213563 11/1987 European Pat. Off. .

OTHER PUBLICATIONS

Medi-tech Catalog, copyright 1989, p. 911, entitled "Segura Baskets".
Microvasive Catalog, dated 1989, pp. 51-61, entitled "Segura Baskets".

Primary Examiner—Edgar S. Burr
Assistant Examiner—Christopher A. Bennett
Attorney, Agent, or Firm—Emil Richard Skula

[57] ABSTRACT

An applicator is provided for applying a sheet of surgical material, e.g., an adhesion barrier or other surgical fabric, to internal body tissue. The applicator includes an expandable operating tip which is insertable into an endoscopic tube through an incision in a body to enable a surgeon to apply the adhesion barrier or other surgical fabric to tissue inside the body. A preferred embodiment of the applicator includes a set of telescoping tubes comprising an outer delivery tube, a intermediate deployment tube, and a inner irrigation tube. An expandable spreader tip is mounted at the distal end of the irrigation tube and connected to the distal end of the deployment tube. By advancing the deployment tube and irrigation tube relative to the delivery tube, the spreader tip is exposed at the distal end of the delivery tube. The spreader tip is expanded by movement of the deployment tube relative to the irrigation tube to spread the adhesion barrier over the tissue. A nozzle is provided at the distal end of the irrigation tube for applying a fluid, e.g., a saline solution, to the adhesion barrier.

40 Claims, 12 Drawing Sheets

ADHESION BARRIER APPLICATOR

This is a continuation of application Ser. No. 07/779,432, filed Oct. 18, 1991, now abandoned.

FIELD OF THE INVENTION

The present invention relates to an applicator adapted for applying a sheet of surgical material such as an adhesion barrier to tissue in a human body and, more particularly, to an adhesion barrier applicator including an expandable operating tip which is insertable into the body through an incision to enable a surgeon to apply an adhesion barrier to tissue inside the body. The delivery device is particularly suitable for spreading an absorbable adhesion barrier over internal body tissue, e.g., the ovaries or uterus, following surgery, to reduce the incidence of post-operative adhesions.

BACKGROUND OF THE INVENTION AND PRIOR ART

Surgical procedures have been developed for performing gynecologic pelvic surgery by using an operating laparoscope which is inserted into a trocar tube or sleeve extending through an incision in the body into the pelvic area. The operating laparoscope includes a separate optical passage for viewing the surgical area and an operating channel for the passage of instruments or a laser beam to perform surgery on the tissue inside the body. Also, most surgical procedures require the use of ancillary trocar tubes for passage of additional surgical instruments. Typically, a trocar is inserted into the trocar sleeve to facilitate the insertion of the trocar sleeve through an incision and its penetration through the body wall. After the trocar sleeve is positioned at a desired surgical site, the trocar is removed from the trocar sleeve to allow the operating laparoscope to be inserted into the trocar sleeve and advanced into position to view the surgical site. Then, the additional ancillary trocar ports are created, as necessary, to support the surgical procedure. The desired surgery is performed by inserting an operating instrument, e.g., grasping forceps or scissors, into the appropriate trocar port.

After the surgical procedure is performed, an adhesion barrier is applied to the surgical site to reduce the adhesion formation at the site. The adhesion barrier is applied to the traumatized tissue surfaces after hemostasis to physically separate opposing tissue surfaces during the period of repair or reperitonealization of the tissue. The adhesion barrier consists of material which is absorbable by the body tissue at the site of implantation. For example, an adhesion barrier known as INTERCEED TM (TC-7) Absorbable Adhesion Barrier has been developed by Johnson & Johnson which consists of an absorbable knitted fabric composed of oxidized regenerated cellulose.

In the prior art procedure, the installation of the adhesion barrier is performed by using a grasping forceps which is inserted into the channel in the operating laparoscope. Before the insertion of the grasping forceps, the operating laparoscope is removed from the trocar sleeve and cleaned if blood or fluid is present. The grasping forceps is inserted into the operating channel and used to grasp one corner of the adhesion barrier beyond the distal end of the laparoscope. Then, the forceps is drawn backward to pull the adhesion barrier into the operating channel until the adhesion barrier is enclosed within the distal end of the laparoscope. Next, the laparoscope is again inserted into the body via the trocar sleeve and positioned over the desired application area. The grasping forceps is pushed into the operating laparoscope to push the adhesion barrier into the body cavity. Thereafter, by using additional grasping instruments inserted into the body through separate trocar sleeves or tubes, the surgeon can manipulate the adhesion barrier into the desired placement over the traumatized tissue, .e.g., a peritoneal defect. After placement on the tissue, the adhesion barrier is moistened with irrigation fluid, e.g., a saline solution.

The installation procedure of the prior art requires the surgeon to perform a complicated series of steps including the removal and cleaning of the laparoscope, the insertion of the grasping forceps into the operating channel to grasp the adhesion barrier at the distal end of the laparoscope, the retraction of the forceps and the adhesion barrier into the laparoscope, the reinsertion of the laparoscope into the trocar sleeve, and the manipulation of the adhesion barrier at the surgical site by using additional grasping instruments inserted into the body through additional trocar sleeves or tubes. These steps are time consuming and the required manipulation of the adhesion barrier is difficult to perform due to the limited space inside the body.

In the prior art, it is known to utilize an inserter device for the purpose of installing an absorbant tampon in the internal vaginal cavity. For example, U.S. Pat. No. 3,857,395 discloses an inserter device which includes a pair of outwardly bendable arms which bilaterally spread the tampon within the vaginal cavity. However, the disclosed inserter device is not suitable for insertion into a laparoscope for applying an adhesion barrier through a trocar sleeve or tube to an application area where surgery has been performed.

In addition, other types of instruments are known in the prior art for manipulating internal body tissue. For example, U.S. Pat. No. 4,909,789 discloses observation assisting forceps including a set of expandable wires mounted on a shaft which is normally retracted into a sheath. When the shaft is advanced, the wires project out of the sheath and expand into a fan-shaped configuration in the same plane. The expanded wires can be used to set aside internal organs obstructing the observation with an abdominal cavity endoscope. The wires are provided at the tips with spherical members which prevent the organs from being hurt.

U.S. Pat. No. 4,654,028 discloses an incision opening expansion holder including a plurality of wires at the end of an inner tube which are three dimensionally expanded when projecting out of an outer tube to expand an incision of a blood vessel graft for purposes of inosculation. U.S. Pat. No. 4,705,041 discloses a tissue dilator comprising a catheter which supports an expandable member, e.g., a balloon or a scissor-like member. U.S. Pat. No. 1,878,671 discloses a dilator for opening a body cavity including an ovate head mounted on a wire received in a tube which is inserted into the body cavity. U.S. Pat. No. 4,655,219 discloses a tissue grasping accessory including a plurality of flexible grasping arms for use with an endoscopic instrument to grasp a tissue specimen. U.S. Pat. No. 4,590,938 discloses a device for removal of kidney stones through the working channel of an endoscope including a basket comprising four outwardly bowed, generally flat spring arms which are expandable into a bulbous shape and collapsed when retracted into a sheath. The relatively broad, flat surfaces of the spring strips deflect the kidney tissue surrounding the stone while the distally enlarged volume of the basket allows the surgeon to dislodge and capture the stone.

None of the above described devices are particularly suited for use in applying and spreading a sheet of surgical material, e.g., an adhesion barrier, through an endoscopic tube to traumatized tissue after surgery. Moreover, it appears that several of the devices may have a tendency to damage the tissue if attempted to be used to install an adhesion barrier over internal body tissue.

Accordingly, it is an object of the present invention to provide an applicator which is adapted to simplify the application of a sheet of surgical material such as an adhesion barrier to internal body tissue.

Another object of the invention is to provide an applicator to facilitate the installation of a sheet of surgical material such as an adhesion barrier through an endoscopic tube to tissue in a body cavity.

It is also an object of the invention to provide an adhesion barrier applicator which is suitable for insertion through an endoscopic tube and is adapted to spread the adhesion barrier over the tissue application area to minimize the need for manipulation of the adhesion barrier by separate grasping instruments.

SUMMARY OF THE INVENTION

The present invention achieves an applicator which is adapted for insertion through a trocar sleeve or tube to apply a sheet of surgical material such as an adhesion barrier to internal body tissue. The applicator can be also used to apply other types of fabrics used in surgery, e.g., topical hemostats, surgical meshes and surgical patches. The invention is embodied in an adhesion barrier applicator comprising a tube, a shaft slidably received within the tube, and an operating tip mounted at the distal end of the shaft and connected to the distal end of the tube for engaging the adhesion barrier. The operating tip is expandable by movement of the shaft relative to the tube to apply the adhesion barrier to the tissue. Preferably, the shaft comprises an irrigation tube for supplying fluid to the adhesion barrier. A nozzle is provided at the distal end of the irrigation tube for discharging the fluid therefrom.

In accordance with the invention, the operating tip of the adhesion barrier applicator includes a plurality of flexible arms extending from the distal end of the shaft to the distal end of the tube. The arms are flexed outwardly when the tube is displaced relative to the shaft to spread the adhesion barrier onto the tissue. Each of the flexible arms has an intermediate portion which bulges laterally outward when the arm is flexed for spreading the adhesion barrier onto the tissue. Preferably, the arms are spaced circumferentially apart about the operating tip. When the operating tip is actuated, the arms flex laterally outward into a convex shape and also into a concave shape at the distal end of the operating tip to spread the adhesion barrier over the tissue.

A preferred embodiment of the adhesion barrier applicator adapted for insertion into an endoscopic tube, e.g., an operating laparoscope or a trocar tube or sleeve at an ancillary site, to apply an adhesion barrier to internal body tissue, includes a delivery tube sized for insertion into the endoscopic tube, a deployment tube slidably received within the delivery tube, a support shaft slidably received within the deployment tube, and an expandable spreader tip mounted at the distal end of the support shaft and connected to the distal end of the deployment tube for engaging the adhesion barrier. The spreader tip assumes a collapsed configuration upon insertion into the delivery tube with the adhesion barrier thereon.

In accordance with one aspect of the present invention, the preferred embodiment of the adhesion barrier applicator includes actuator means for advancing the deployment tube and the support shaft together relative to the delivery tube to expose the spreader tip and the adhesion barrier at the distal end of the delivery tube. The adhesion barrier applicator also includes means for stopping the advancement of the support shaft with the spreader tip and adhesion barrier exposed. The spreader tip is expandable by movement of the deployment tube relative to the support shaft to apply the adhesion barrier to the tissue.

In accordance with another aspect of the invention, the preferred embodiment of the adhesion barrier applicator includes means for releaseably holding the deployment tube in the delivery tube to retain the spreader tip retracted inside the delivery tube prior to the exposure of the spreader tip therefrom. The adhesion barrier is draped over the spreader tip and held in the delivery tube prior to the exposure of the spreader tip from the distal end of the delivery tube.

In the preferred embodiment of the adhesion barrier applicator the spreader tip includes a plurality of flexible arms extending from the distal end of the support shaft to the distal end of the deployment tube. The arms are flexed outwardly when the deployment tube is advanced relative to the support shaft to spread the adhesion barrier onto the tissue. Each of the flexible arms has an intermediate portion which bulges laterally outward when the arm is flexed for spreading the adhesion barrier onto the tissue. Preferably, the arms are spaced circumferentially apart about the spreader tip. When the spreader tip is actuated, the arms are flexible into a convex shape and also into a concave shape at the distal end of the spreader tip to spread the adhesion barrier over the tissue.

In the preferred embodiment of the adhesion barrier applicator, the support shaft comprises an irrigation tube for supplying fluid to the adhesion barrier. A nozzle is provided at the distal end of the irrigation tube for discharging the fluid therefrom. Preferably, the applicator is provided with means for connecting the irrigation tube to an external source of fluid. In an alternative form, the adhesion barrier applicator is provided with a reservoir mounted on its handle for supplying fluid to the irrigation tube. Preferably, the reservoir is slidably mounted on the handle for movement with the irrigation tube. A pump is slidably mounted on the handle for movement with the reservoir for pumping fluid from the reservoir to the irrigation tube.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF PREFERRED EMBODIMENTS

Figure 1:
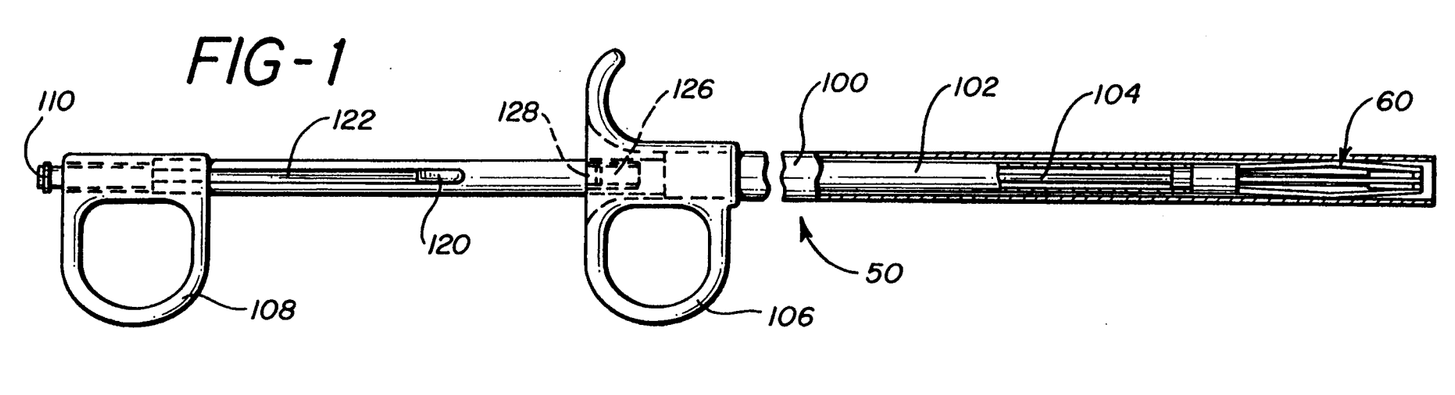
FIG. 1 is a partially cutaway side view of an adhesion barrier applicator constructed in accordance with this invention.
Figure 2:
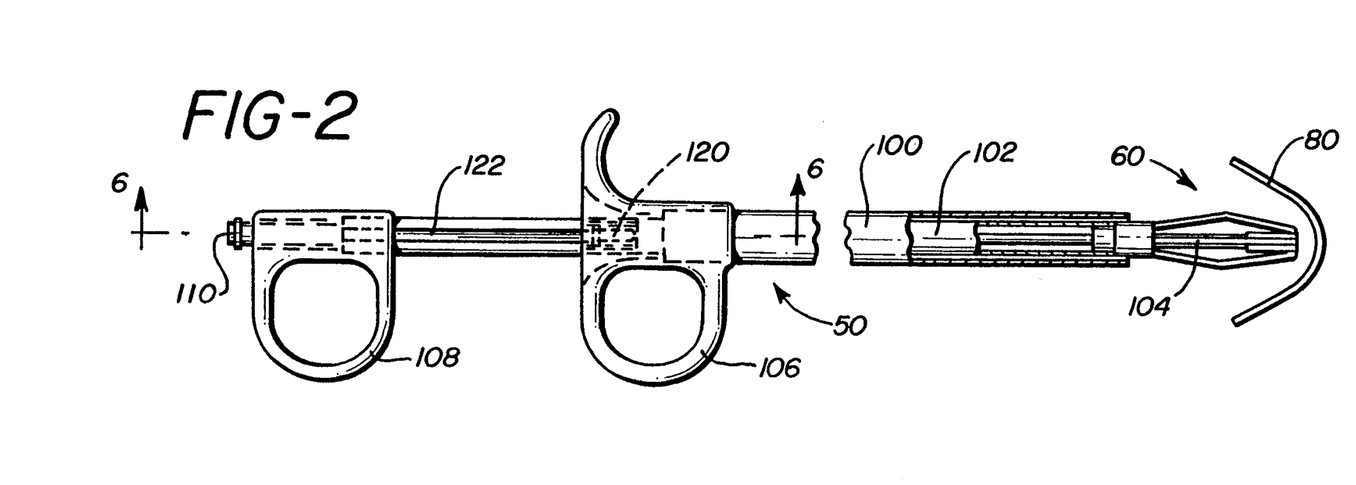
FIG. 2 is a partially cutaway side view of the applicator of FIG. 1 with its operating tip exposed.

Referring to FIG. 1, the present invention is embodied in an applicator or delivery device, generally 50, including an expandable operating tip 60 which is insertable through an incision or a natural body orifice to enable a surgeon to apply a sheet of surgical material, such as an adhesion barrier 80 (FIG. 2), to tissue inside the body. The applicator 50 is particularly suitable for use by a surgeon to spread the adhesion barrier 80 over internal body tissue, e.g., the ovaries or uterus, after gynecologic surgery, to prevent the formation of undesirable adhesions.

As shown in FIG. 1, the adhesion barrier applicator 50 includes a set of three elongated tubes 100, 102 and 104 which are telescoped together. Preferably, the outer tube 100 consists of clear plastic material and, if desired, the tubes 102 and 104 are made of the same material. The outer tube 100 is secured at its proximal end to a finger grip 106. The outer tube 100 constitutes a delivery tube through which the operating tip 60 is inserted into the body. The intermediate tube 102 is slidably received by the outer delivery tube 100 and is secured at its proximal end to a finger grip 108. The intermediate tube 102 serves as a deployment tube for actuating the operating tip 60 and applying the adhesion barrier 80 inside the body. The inner tube 104 is slidably received within the deployment tube 102 and extends beyond the distal end of the tube 102. Preferably, the inner tube 104 is a hollow shaft and serves as an irrigation tube for supplying fluid to the operating tip 60.

Figures 3, 4:
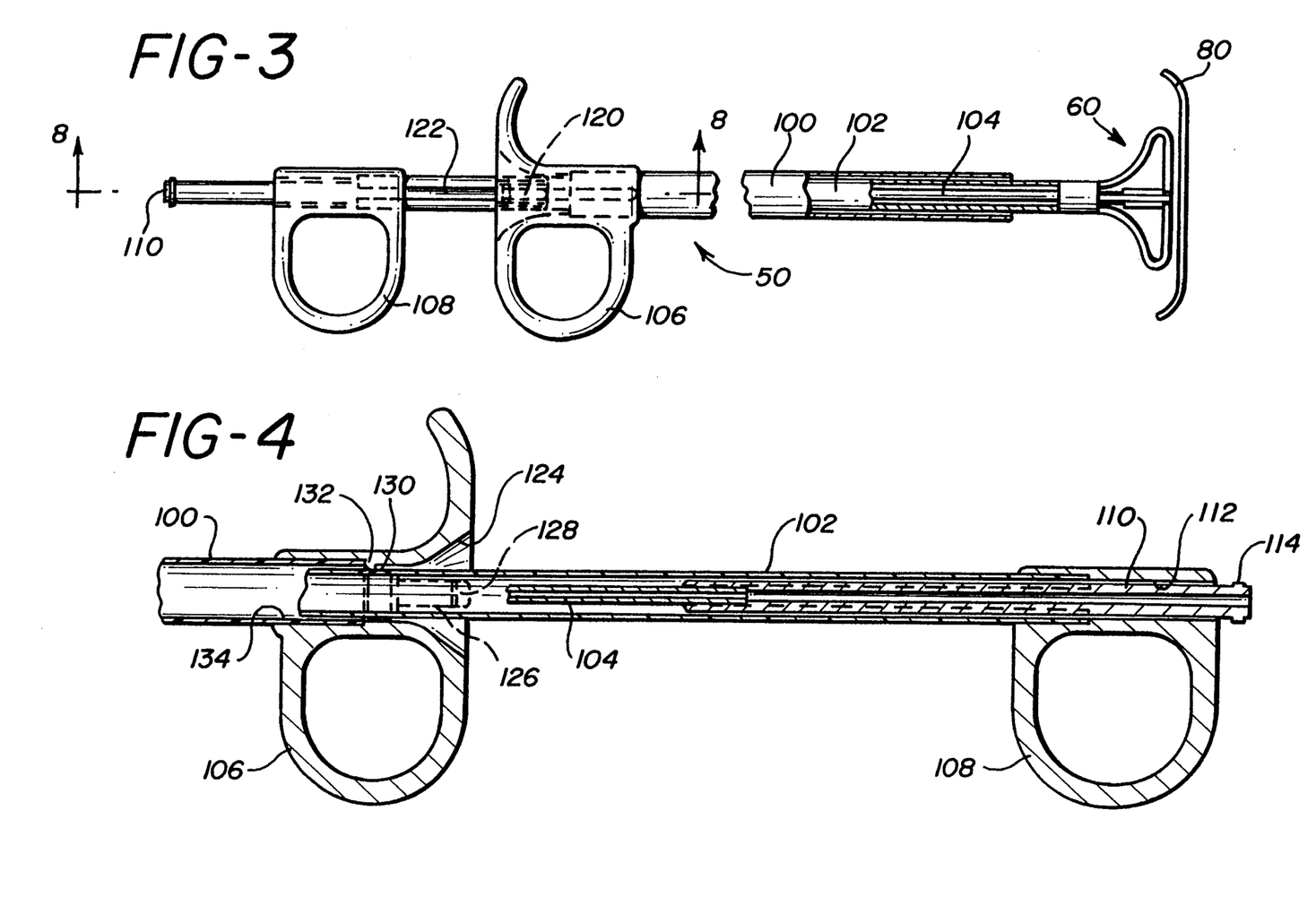
FIG. 3 is a partially cutaway side view of the applicator of FIG. 1 with its operating tip expanded.
FIG. 4 is an enlarged longitudinal section of the proximal end of the applicator from opposite side of FIG. 1.
Figure 5:
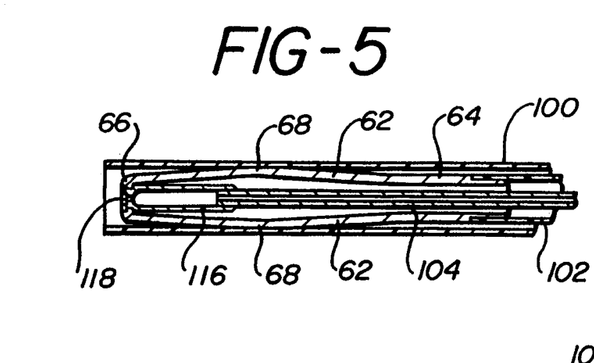
FIG. 5 is an enlarged partially cutaway view of the distal end of the applicator showing the operating tip retracted.

Referring to FIG. 4, the inner irrigation tube 104 is connected at its proximal end to an elongated tubular sleeve 110 which projects proximally outward from the deployment tube 102 and extends through a passage 112 in the finger grip 108. The tubular sleeve 110 has an annular flange 114 at its proximal end for connection to a source of pressurized fluid (not shown) for supplying a saline solution or other fluid to the irrigation tube 104. As shown in FIG. 5, a nozzle 116 is attached to the distal end of the irrigation tube 104. A tip 118 of the nozzle 116 has an orifice for discharging a spray of fluid on the adhesion barrier 80.

Figure 6:
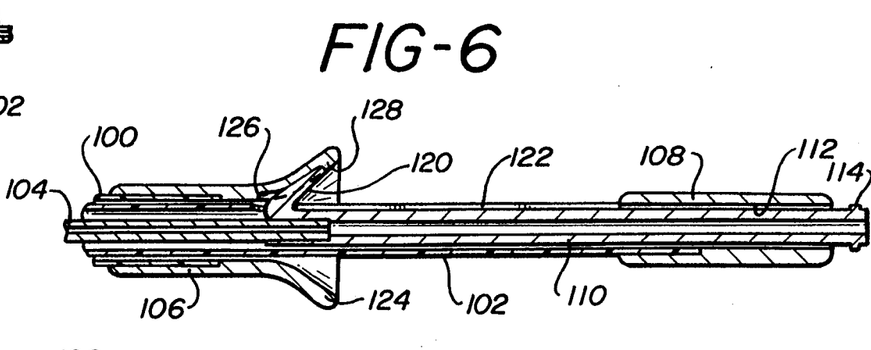
FIG. 6 is an enlarged horizontal section of the applicator along line 6—6 of FIG. 2.

At the distal end of the tubular sleeve 110, a latching finger 120, shown in FIGS. 1 and 6, projects laterally outward through an elongated slot 122 extending along the side of the deployment tube 102. The finger grip 106 includes a funnel-shaped flange 124 (FIG. 6) which facilitates the insertion of the operating tip 60 and the tubes 102 and 104 into the delivery tube 100. The funnel-shaped flange 124 has an inside notch 126 which provides a detent 128 for engaging and holding the latching finger 120 when the tubular sleeve 110 is advanced into the funnel-shaped flange 124. Also, the deployment tube 102 includes an annular flange 130 (FIG. 4) for engaging a detent 132 formed within a passage 134 of the finger grip 106. With the flange 130 in engagement with the detent 132, the operating tip 60 (FIG. 5) is retained in a retracted position within the distal end of the delivery tube 100.

Figure 7:
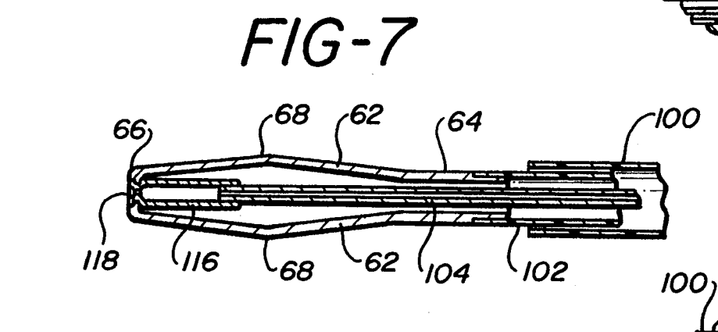
FIG. 7 is an enlarged partially cutaway side view showing the operating tip exposed.
Figure 8:
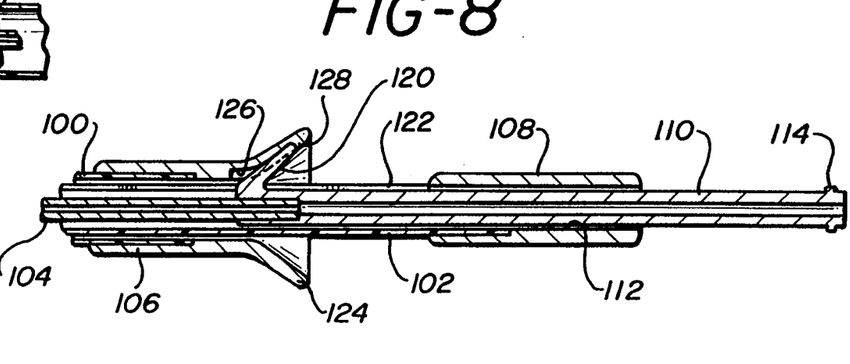
FIG. 8 is an enlarged horizontal section of the applicator along line 8—8 of FIG. 3.
Figure 11:
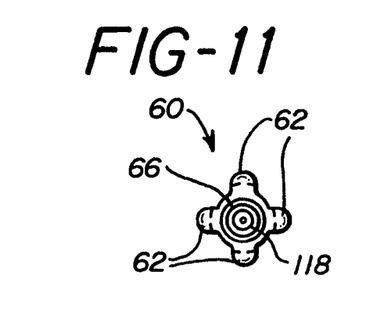
FIG. 11 is an end view of the operating tip in a collapsed configuration.
Figure 12:
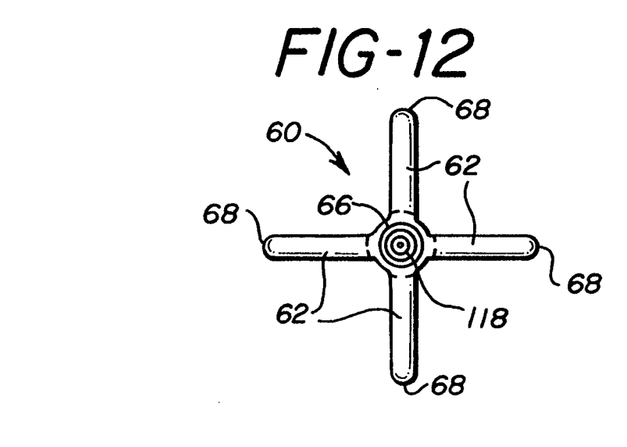
FIG. 12 is an end view of the operating tip in an expanded configuration.

Referring to FIG. 7, the operating tip 60 comprises an expandable basket-like frame or spreader made of flexible material such as rubber or plastic. The spreader includes a plurality of flexible frame members or strips 62 extending longitudinally from an integrally formed sleeve 64 attached to the distal end of the deployment tube 102. The frame members or strips 62 terminate in an annular collar 66 located at the distal end of the operating tip 60 and attached to the tip 118 of the spray nozzle 116. In the relaxed or collapsed configuration of the operating tip 60, each strip 62 is slightly bent and extends radially outward at its midpoint 68 away from the irrigation tube 104. As shown in FIG. 11, the longitudinal strips 62 are spaced circumferentially about the operating tip 60 at equal intervals. For example, the four strips 62 are spaced apart at intervals of 90 degrees.

Referring to FIG. 4, the operating tip 60 is actuated by grasping and squeezing the finger grips 106 and 108 together to advance the deployment tube 102 and the irrigation tube 104 distally relative to the delivery tube 100. When the annular flange 130 engages the detent 132, the operating tip 60 (FIG. 5) is temporarily retained in a retracted position at the distal end of the delivery tube 100. By squeezing the finger grips 106 and 108 together with sufficient force, the annular flange 130 is advanced distally beyond the detent 132 and the tubes 102 and 104 are advanced until the latching finger 120 engages the detent 128 on the funnel-shaped flange 124 to stop the tube 104. By further squeezing of the finger grips 106 and 108 together, the operating tip 60 is expanded as the deployment tube 102 is advanced relative to the irrigation tube 104.

Figure 9:
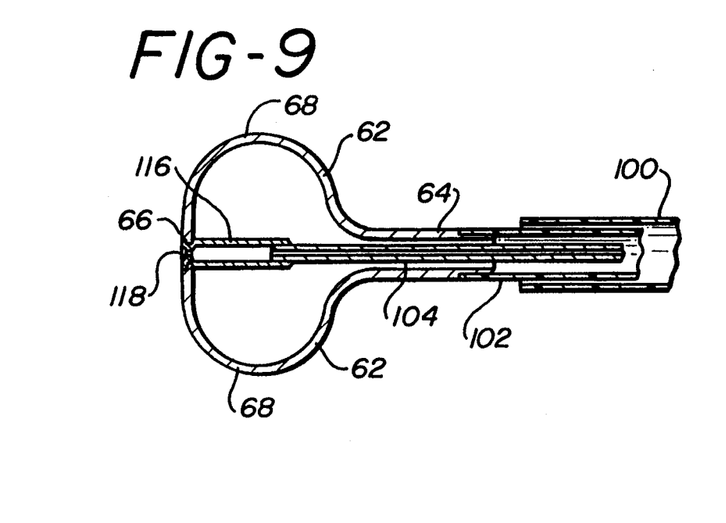
FIG. 9 is an enlarged partially cutaway side view of the operating tip in a convex shape.
Figure 10:
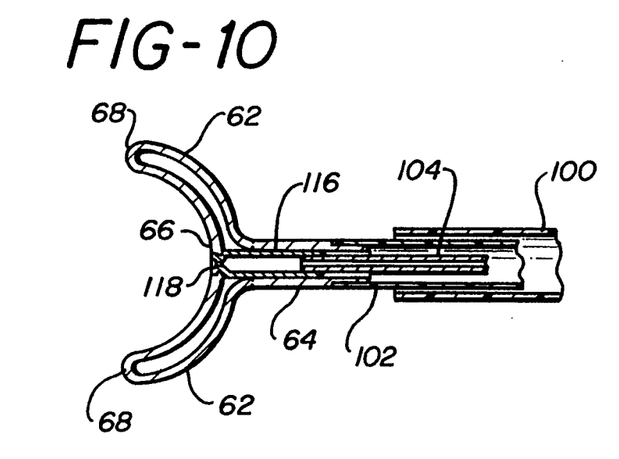
FIG. 10 is an enlarged partialy cutaway side view of the operating tip in a concave shape.

During the expansion of the operating tip 60, the longitudinal arms 62 are flexed outwardly at the midpoints 68 by movement of the sleeve 64 toward the distal end of the irrigation tube 104. As shown in FIG. 9, the elongated arms 62 are flexed into a convex shape by the advancement of the sleeve 64 along the irrigation tube 104. As shown in FIG. 10, the front portion of the operating tip 60 assumes a concave shape as the sleeve 64 is advanced closer to the distal end of the irrigation tube 104.

Figure 13:
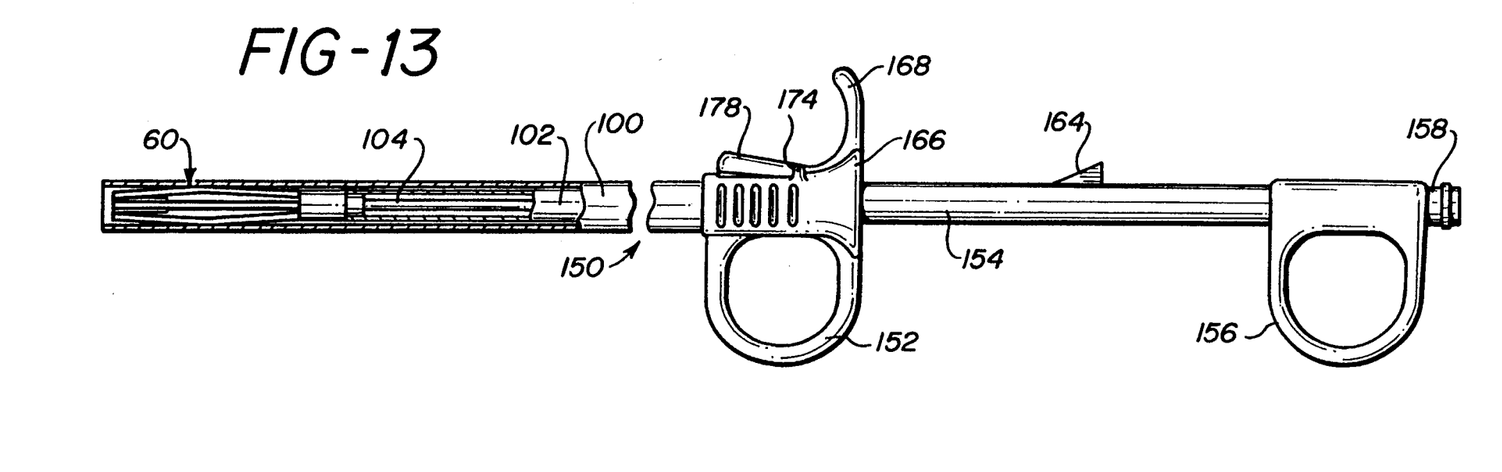
FIG. 13 is a partially cutaway side view of an alternative embodiment of the adhesion barrier applicator of the present invention.

Referring to FIG. 13, an alternative embodiment of the adhesion barrier applicator, generally 150, includes the same operating tip 60 and the same arrangement of telescoping tubes 100, 102 and 104 described above. The delivery tube 100 is secured at its proximal end to a finger grip 152. The delivery tube 100 slidably receives the deployment tube 102 which, in turn, slidably receives the irrigation tube 104. The deployment tube 102 is secured at its proximal end to a tubular sleeve 154 which, in turn, is secured to a finger grip 156.

Figure 16:
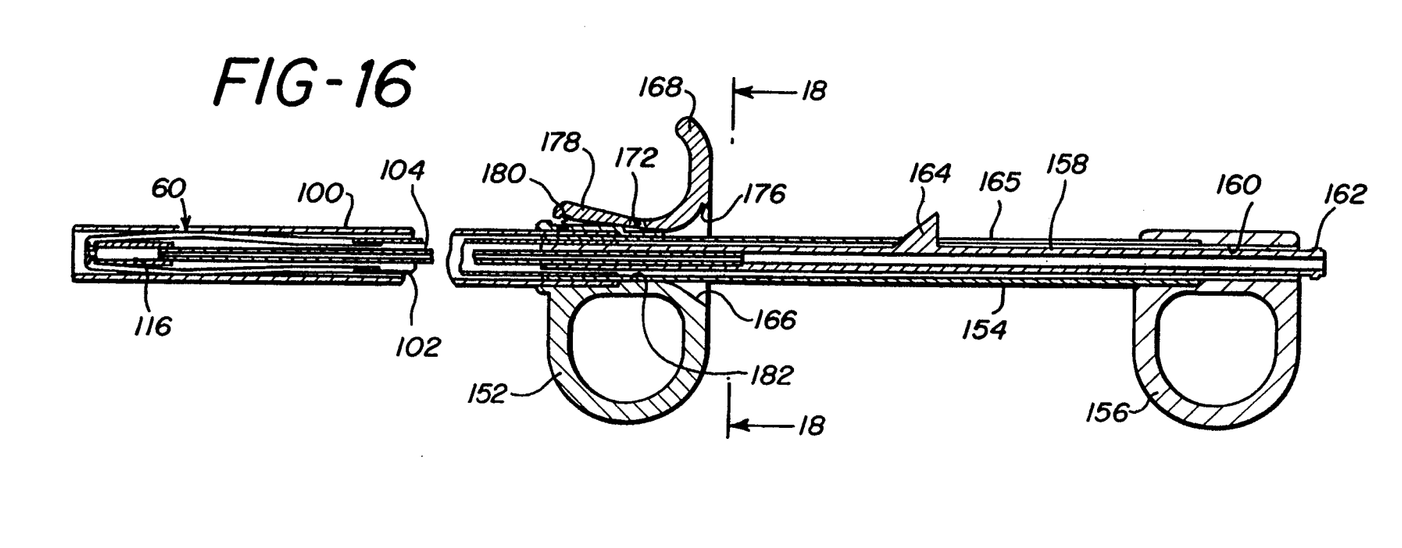
FIG. 16 is an enlarged longitudinal section of the adhesion barrier applicator of FIG. 13.
Figure 17:
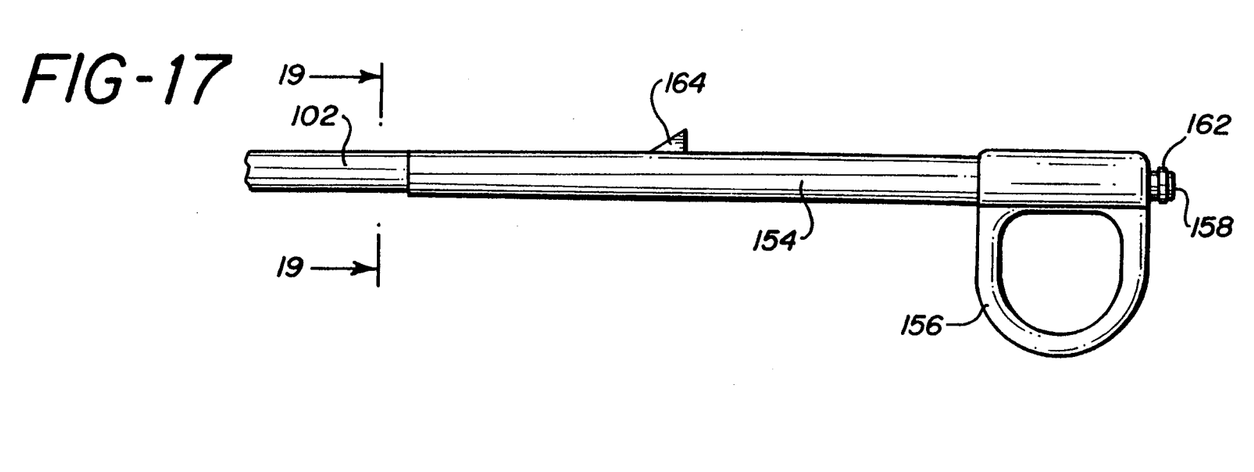
FIG. 17 is a partially cutaway side view of a deployment tube removed from the adhesion barrier applicator of FIG. 13.

Referring to FIG. 16, the inner irrigation tube 104 is connected at its proximal end to an elongated tubular Shaft 158 which projects proximally outward from the deployment tube 102 and extends through a passage 160 in the finger grip 156. The tubular shaft 158 has an annular flange 162 at its proximal end for connection to a source of pressurized fluid (not shown) for supplying a saline solution or other fluid to the irrigation tube 104. The fluid is supplied by the irrigation tube 104 to the nozzle 116 of the operating tip 60.

Figure 14:
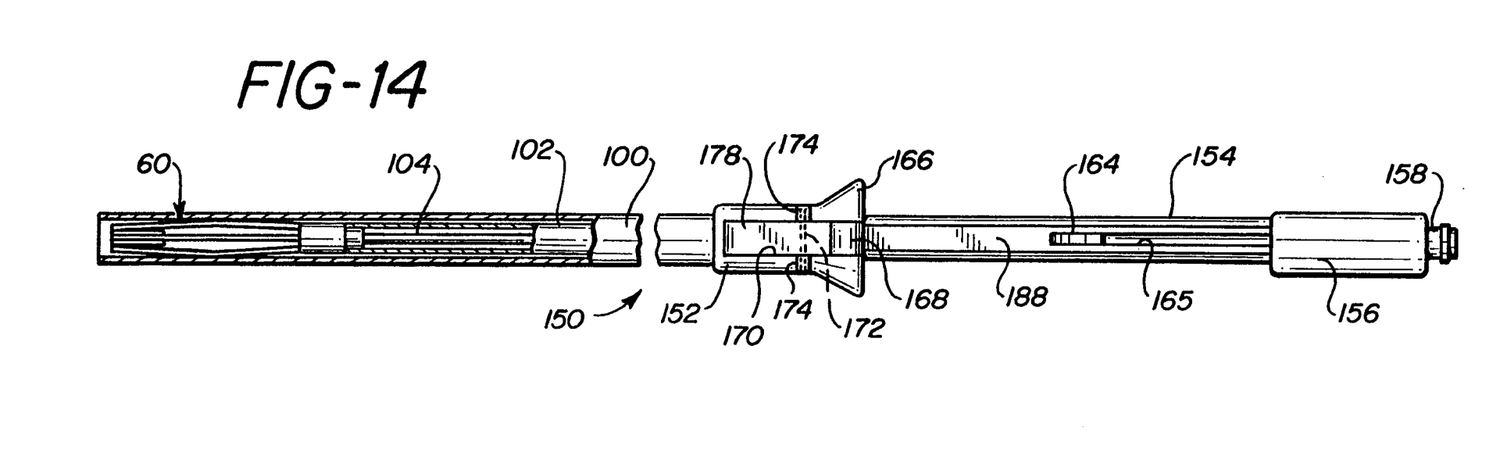
FIG. 14 is a partially cutaway top view of the adhesion barrier applicator of FIG. 13.

At the top of the tubular shaft 158, a latching finger 164 projects upwardly through an elongated slot 165 (FIG. 14) extending along the top of the tubular sleeve 154. The finger grip 152 includes a funnel-shaped flange 166 which facilitates the insertion of the operating tip 60 and the tubes 102 and 104 into the delivery tube 100. A latch arm 168 (FIG. 16) is pivotally mounted on the finger grip 152 in a longitudinal slot 170 (FIG. 14) extending along the top of the finger grip 152 into the funnel-shaped flange 166. The latch arm 168 is mounted on a pivot pin 172 which extends transversely between a pair of lugs 174 located on opposite sides of the finger grip 152.

As shown in FIG. 16, the latch arm 168 projects upwardly from the finger grip 152 to provide a finger rest for engagement by the index finger of the surgeon. A detent 176 is provided on the latch arm 168 for engaging the latching finger 164 when the deployment tube 102 and the irrigation 104 are advanced to expose the operating 60 at the distal end of the delivery tube 100. The latch arm 168 has a release lever 178 at its distal end which is biased upwardly from the finger grip 152 by a spring 180. The detent 176 on the latch arm 168 is urged downwardly by the spring 180 for engagement with the latching finger 164.

When the deployment tube 102 and irrigation tube 104 are advanced into the delivery tube 100, the latch arm 168 serves as a stop which engages the latching finger 164 to stop the advancement of the irrigation tube 104 with the operating tip 60 exposed from the distal end of the delivery tube 100. By further movement of the deployment tube 102 relative to the irrigation tube 104, the operating tip 60 is expanded to apply the adhesion barrier 80 to the tissue. After the adhesion barrier 80 is set in place, the deployment tube 102 is retracted by pulling on the finger grip 156 to collapse the operating tip 60. Next, the latching finger 164 is released by pressing on the release lever 178 of the latch arm 168 to disengage the detent 176 from the latching finger 164. Then, by pulling on the finger grip 156, the deployment tube 102 and the irrigation tube 104 are retracted to withdraw the operating tip 60 into the distal end of the delivery tube 100.

Figure 18:
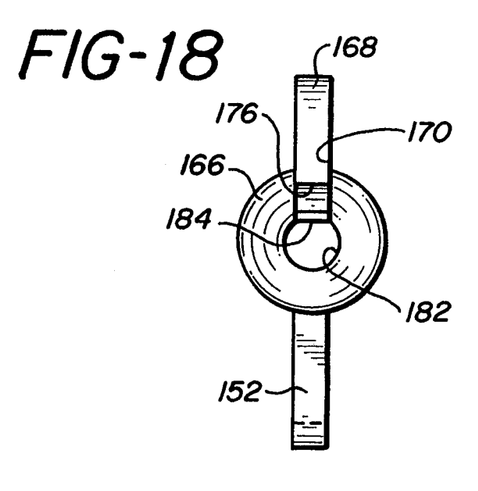
FIG. 18 is an end view along line 18—18 of FIG. 16 with the deployment tube removed from the adhesion barrier applicator.
Figure 19:
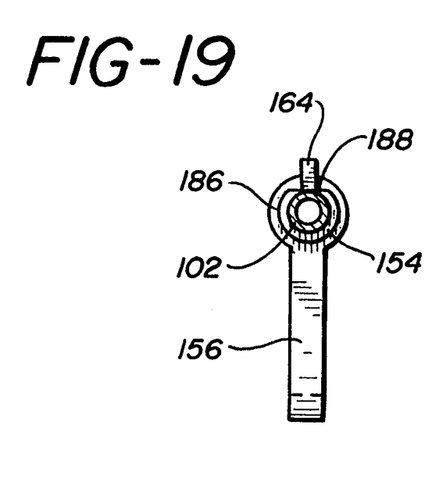
FIG. 19 is a cross section of the deployment tube along line 19—19 of FIG. 17.

Preferably, the adhesion barrier applicator 150 is adapted to retain the operating tip 60 retracted inside the delivery tube 100 prior to the exposure of the operating tip 60 from the distal end of the delivery tube 100. As shown in FIG. 18, the funnel-shaped flange 166 has a keyway-shaped passage 182 which is substantially circular in cross section except for a flat segment 184 located at the top of the passage. As shown in FIG. 19, the sleeve 154 attached to the proximal end of the deployment tube 102 has a corresponding key-shaped cross section defined by a cylindrical outer surface 186 which is substantially round except for an elongated flat surface 188 at the top of the sleeve 154.

Figure 15:
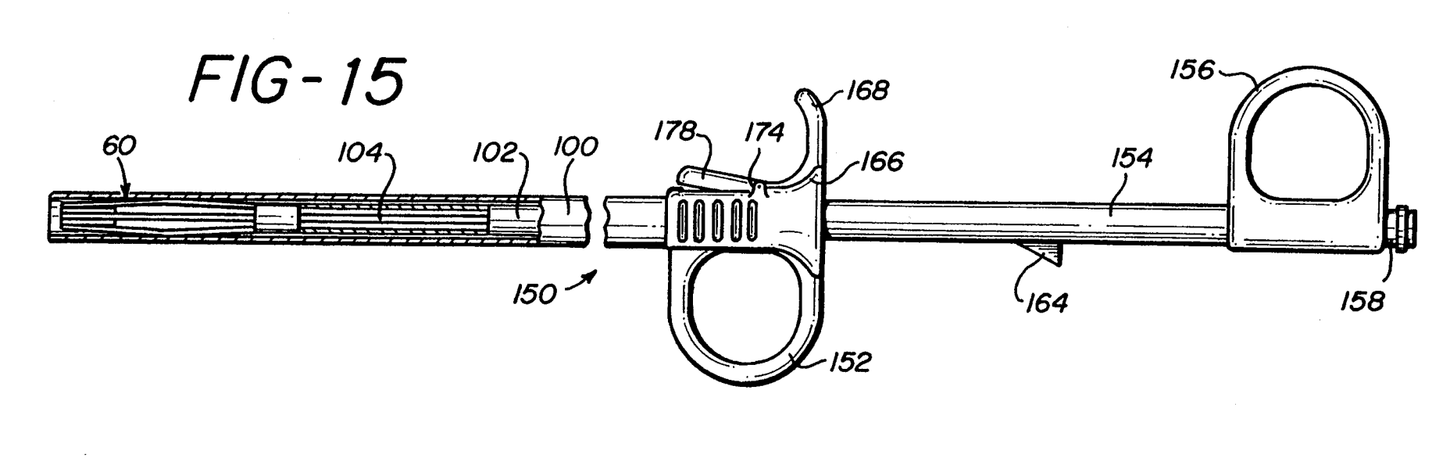
FIG. 15 is a partially cutaway side view of the adhesion barrier applicator of FIG. 13 with its operating tip held in a retracted position.

Referring to FIG. 13, with both finger grips 152 and 154 oriented in the same direction, e.g., downward from the adhesion barrier applicator 150, the key-shaped cross section of the sleeve 154 (FIG. 19) is aligned with the keyway-shaped passage 182 (FIG. 18) to allow the sleeve 154 to slide freely into the passage 182 in the finger grip 152. On the other hand, as shown in FIG. 15, with the finger grips 152 and 154 oriented in different directions, e.g., with the finger grip 152 extending downwardly and the finger grip 156 extending upwardly from the adhesion barrier applicator 150, the key-shaped cross section of the sleeve 154 is misaligned with the keyway-shaped passage 182 to prevent the sleeve 154 from sliding into the passageway 182 in the finger grip 152. As a result, the deployment tube 102 is held in the delivery tube 100 to retain the operating tip 60 inside the distal end of the delivery tube 100. To expose the operating tip 60 from the delivery tube 100, the deployment tube 102 is rotated about its axis to orient the finger grip 156 in the same direction as the finger grip 152 to align the key-shaped sleeve 154 with the keyway-shaped passage 182. Then, the sleeve 154 can be advanced into the passage 182 to advance the deployment tube 102 and expose the operating tip 60 at the distal end of the delivery tube 100.

Figure 20:
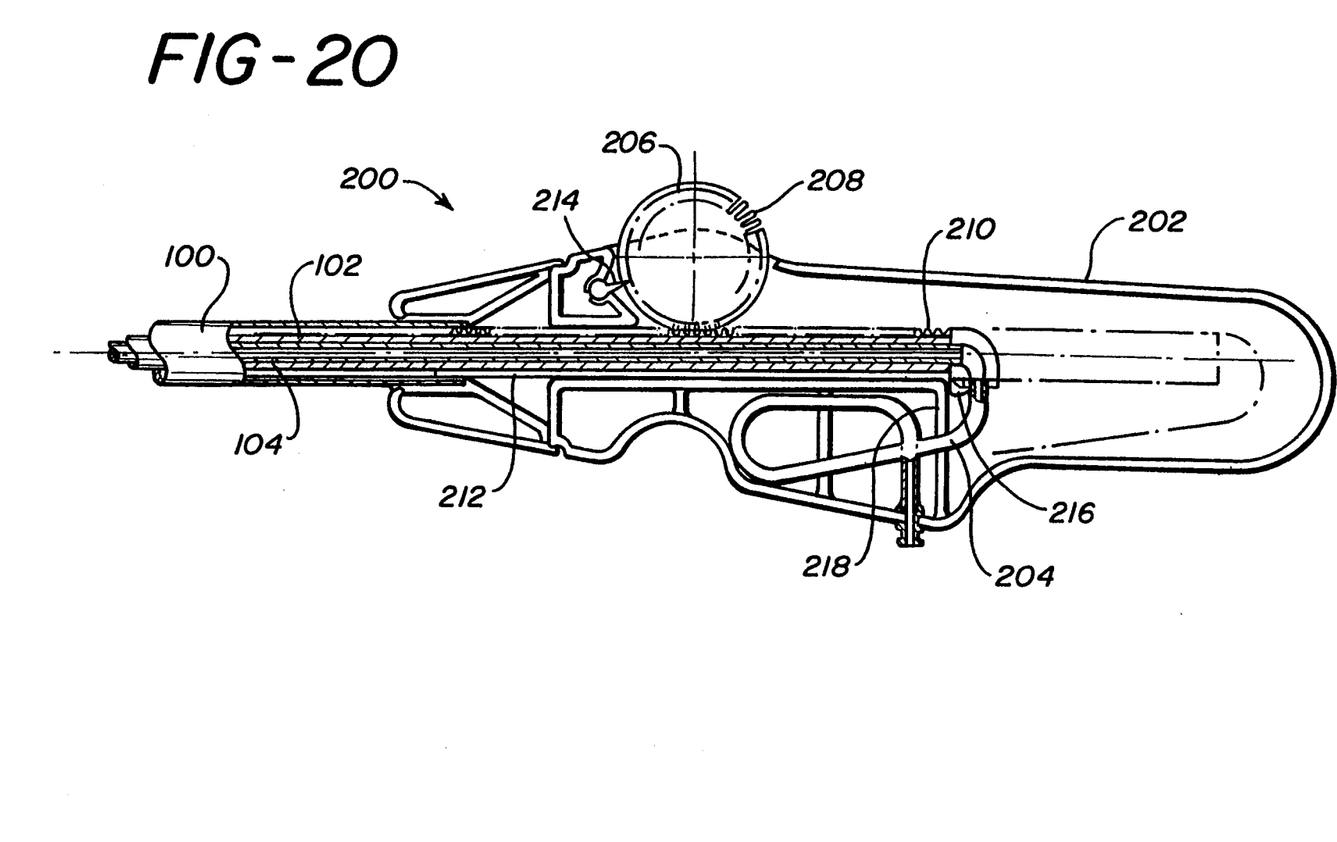
FIG. 20 is a side view partially in section of another embodiment of the applicator.

Referring to FIG. 20, another embodiment of the adhesion barrier applicator, generally 200, includes a handle 202 provided with a flexible tube 204 for attachment to an external source of saline solution. The applicator 200 includes the same operating tip 60 and the same arrangement of telescoping tubes 100, 102 and 104 described above. The delivery tube 100 is secured at its proximal end to the handle 202. The delivery tube 100 slidably receives the deployment tube 102 which, in turn, slidably receives the irrigation tube 104. The flexible tube 204 is attached to the proximal end of the irrigation tube 104 to supply the saline solution to the operating tip 60. The flexible tube 204 allows the irrigation tube 104 to move longitudinally relative to the delivery tube 100 and the handle 202.

The applicator 200 includes a rack and pinion mechanism comprising a rotatable thumb wheel 206 mounted on the handle 202 and provided with a plurality of gear teeth 208 which mesh with a series of gear teeth 210 provided on an extension 212 at the proximal end of the deployment tube 102. By rotation of the thumb wheel 206, the deployment tube 102 and the irrigation tube 104 can be advanced and retracted relative to the delivery tube 100. A ratchet 214 is mounted on the handle 202 for engagement with the gear teeth 208 of the thumb wheel 206. The ratchet 214 allows the deployment tube 102 to be retained in any set position selected by the thumb wheel 206 to hold the operating tip 60 in its expanded configuration.

When the thumb wheel 206 is rotated in a direction to advance the operating tip 60, the deployment tube 102 and the irrigation tube 104 are initially advanced together. A stop 216 (FIG. 20) is provided at the proximal end of the irrigation tube 104 for engaging a rib 218 formed on the handle 202 to stop the advance of the irrigation tube 104 when the operating tip 60 is exposed. By further rotation of the thumb wheel 206, the deployment tube 102 is advanced relative to the irrigation tube 104 to expand the operating tip 60 to apply the adhesion barrier 80 to the tissue application area.

Figure 21:
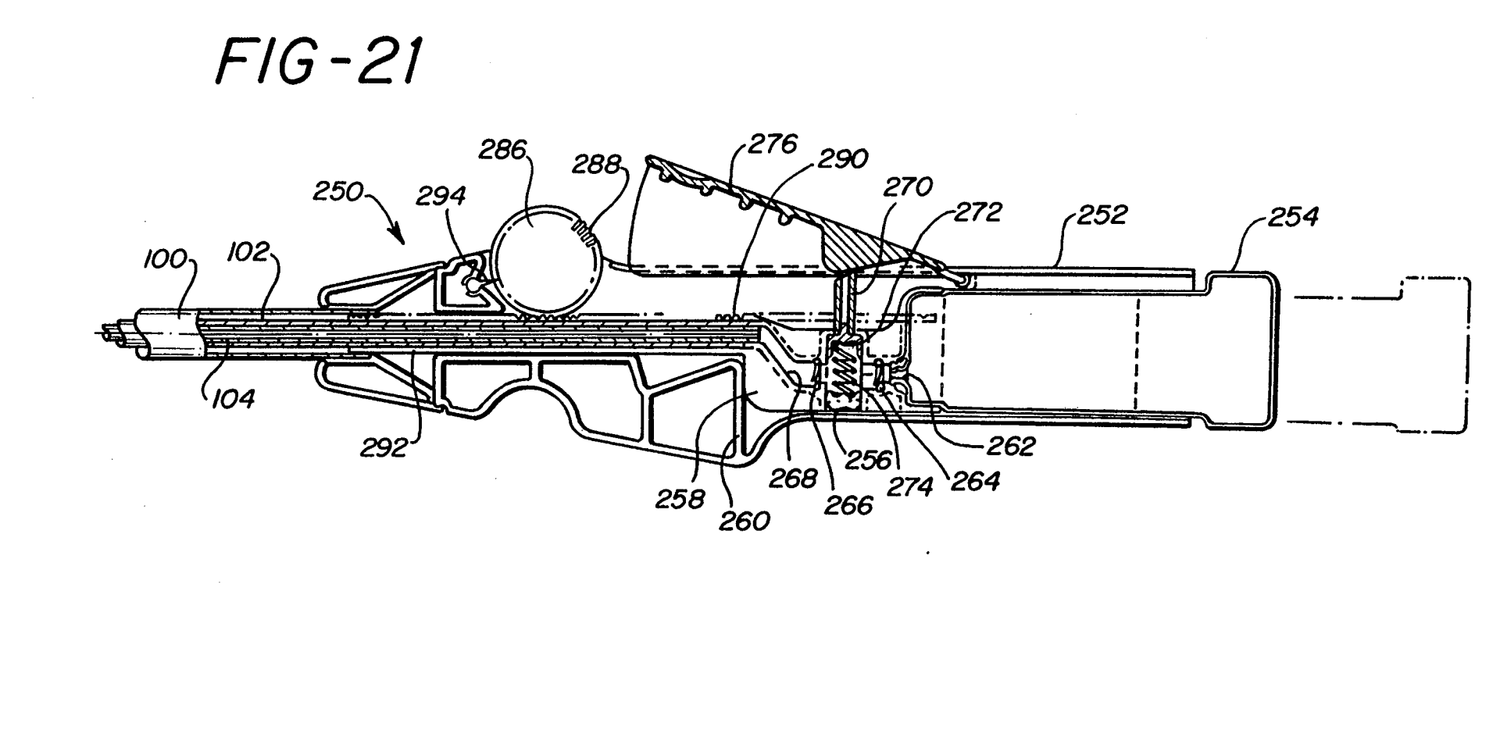
FIG. 21 is a side view partially in section of a further embodiment of the applicator.
Figure 22:
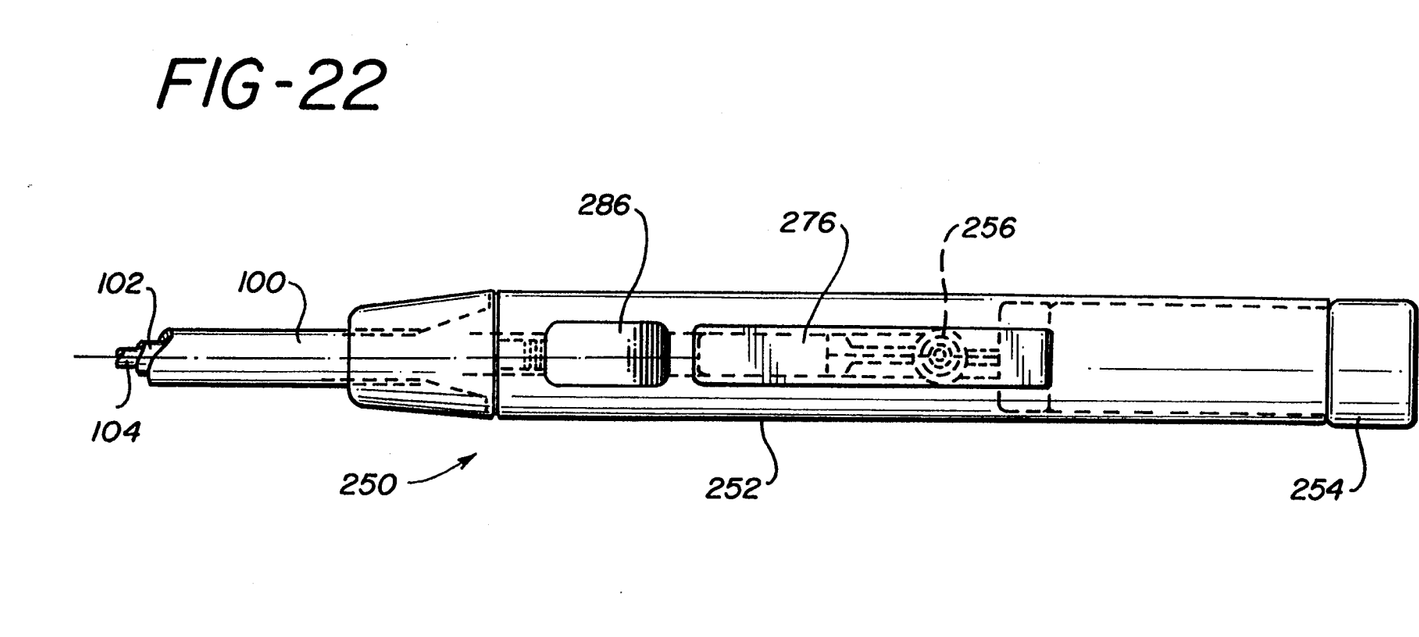
FIG. 22 is a top view of the adhesion barrier applicator of FIG. 21.

Referring to FIG. 21, a further embodiment of the adhesion barrier applicator, generally 250, includes a handle 252 supporting a reservoir 254 for receiving a saline solution. The applicator 250 includes the same operating tip 60 and the same arrangement of telescoping tubes 100, 102 and 104 described above. The delivery tube 100 is secured at its proximal end to the handle 252. The delivery tube 100 slidably receives the deployment tube 102 which, in turn, slidably receives the irrigation tube 104. The reservoir 254 is slidably mounted for longitudinal movement along the handle 252. The reservoir 254 is connected to the irrigation tube 104 through a manually operated pump 256 including a pump housing 258 which is slidable longitudinally relative to the handle 252. A rib 260 is provided on the handle 252 for engaging the pump housing 258 to limit the advancement of the pump 256 and the reservoir 254 relative to the handle 252.

The reservoir 254 includes an outlet 262 for supplying the saline solution through a one-way valve 264 to the pump 256. The saline solution is supplied from the pump 256 through a one-way valve 266 and a fluid passage 268 to the irrigation tube 104. The pump 256 includes a plunger 270 attached to a piston 272 which is biased upward by a spring 274. An irrigation lever 276 is pivotally mounted on the handle 252 for actuating the pump 256. When the lever 276 is depressed, the plunger 270 and piston 272 are driven downward to pump the saline solution from the pump 256 through the one-way valve 266 and passageway 268 into the irrigation tube 104. The saline solution is discharged in the form of a spray from the nozzle 116 (FIG. 7) of the operating tip 60. When the lever 276 is released, the spring 274 returns the plunger 270 and piston 272 upward. The saline solution is drawn from the reservoir 254 through the one-way valve 264 to refill the pump 274.

The applicator 250 includes a rack and pinion mechanism comprising a rotatable thumb wheel 286 mounted on the handle 252 and provided with a plurality of gear teeth 288 which mesh with a series of gear teeth 290 provided on an extension 292 at the proximal end of the deployment tube 102. By rotation of the thumb wheel 286, the deployment tube 102 and the irrigation tube 104 can be advanced and retracted relative to the delivery tube 100. A ratchet 294 is mounted on the handle 252 for engagement with the gear teeth 288 of the thumb wheel 286. The ratchet 294 allows the deployment tube 102 to be retained in any set position selected by the thumb wheel 286 to hold the operating tip 60 in its expanded configuration.

When the thumb wheel 286 is rotated in a direction to advance the operating tip 60, the deployment tube 102 and the irrigation tube 104 are initially advanced together. Since the irrigation tube 104 is connected to the pump housing 258, the pump 256 and the reservoir 254 are advanced with the tube 104 until the pump housing 258 engages the rib 260. The advancement of the irrigation tube 104 is stopped with the operating tip 60 exposed. By further rotation of the thumb wheel 286, the deployment tube 102 is advanced relative to the irrigation tube 104 to expand the operating tip 60 to apply the adhesion barrier 80 to the tissue application area.

Figure 23:
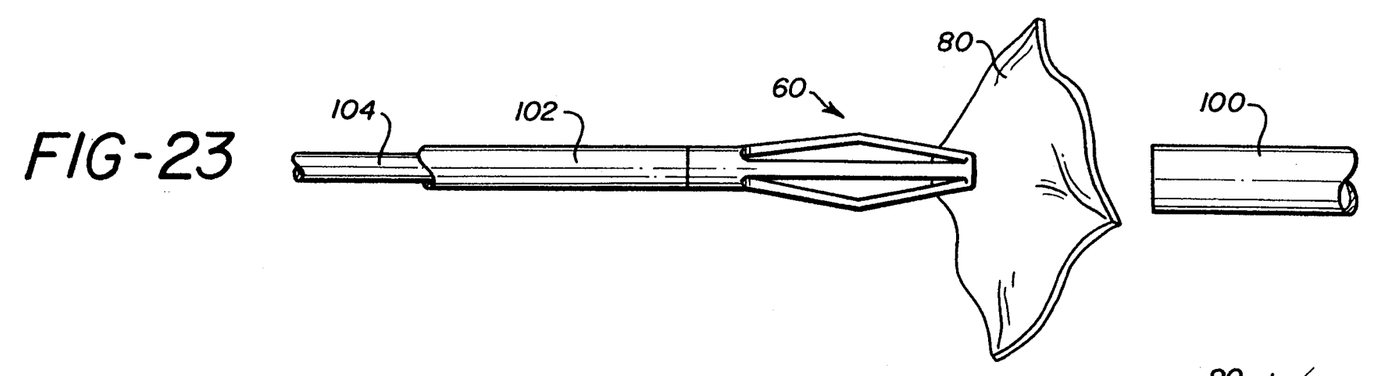
FIGS. 23-28 illustrate the operation of the adhesion barrier delivery device.
Figure 24:
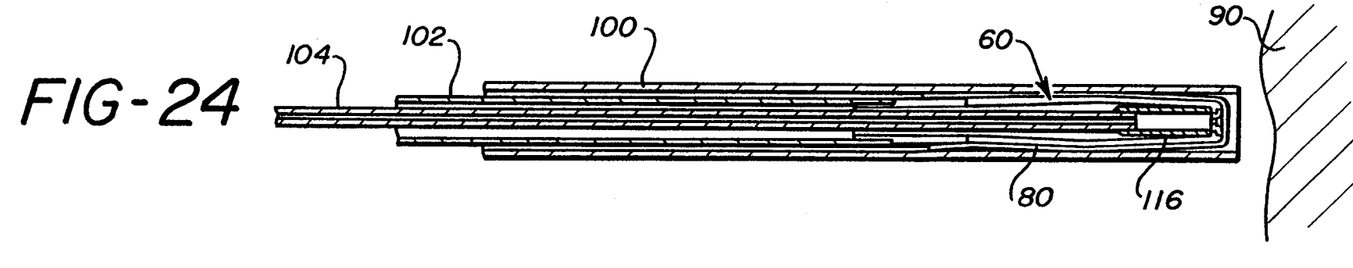

In the operation of the present invention, the adhesion barrier 80 (FIG. 23) is draped over the operating tip 60 in its collapsed configuration. Next, the operating tip 60 and the adhesion barrier 80 are inserted into the delivery tube 100 and advanced by sliding the deployment tube 102 and the irrigation tube 104 along the delivery tube 100 until the operating tip 60 is stopped in a retracted position at the distal end of the delivery tube 100. Then, the delivery tube 100 is inserted into an endoscopic tube extending through an incision in the body and the distal end of the tube 100 is positioned adjacent to the tissue application area 90 where the adhesion barrier 80 is to be applied (FIG. 24).

Figure 25:
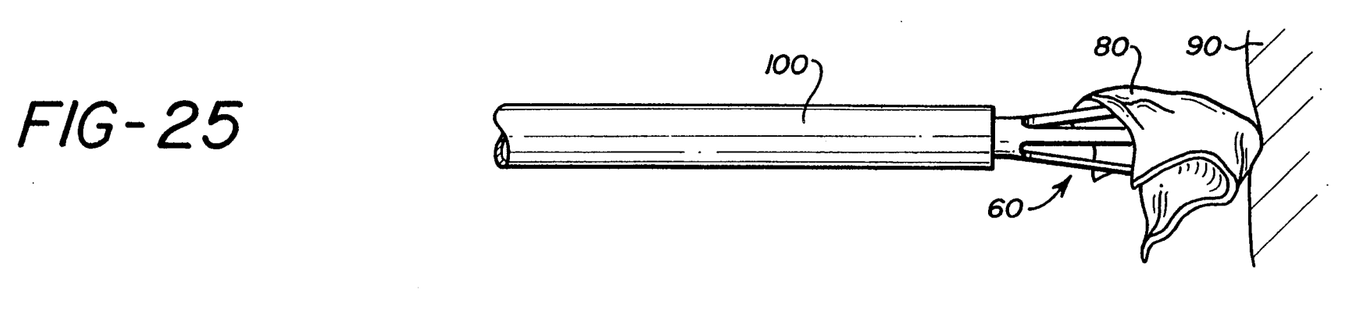
Figure 26:
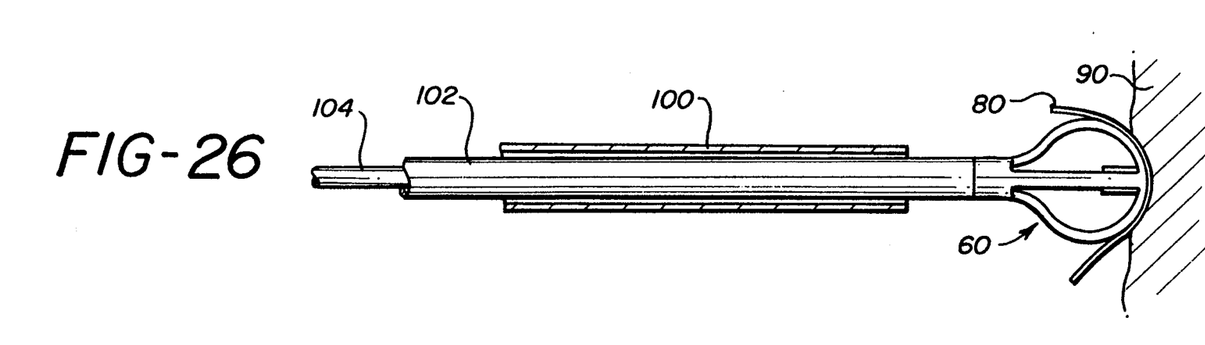
Figure 27:
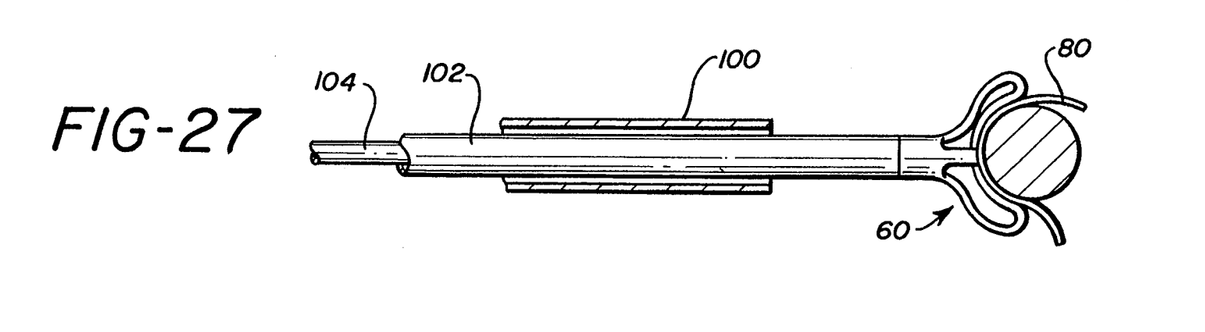
Figure 28:
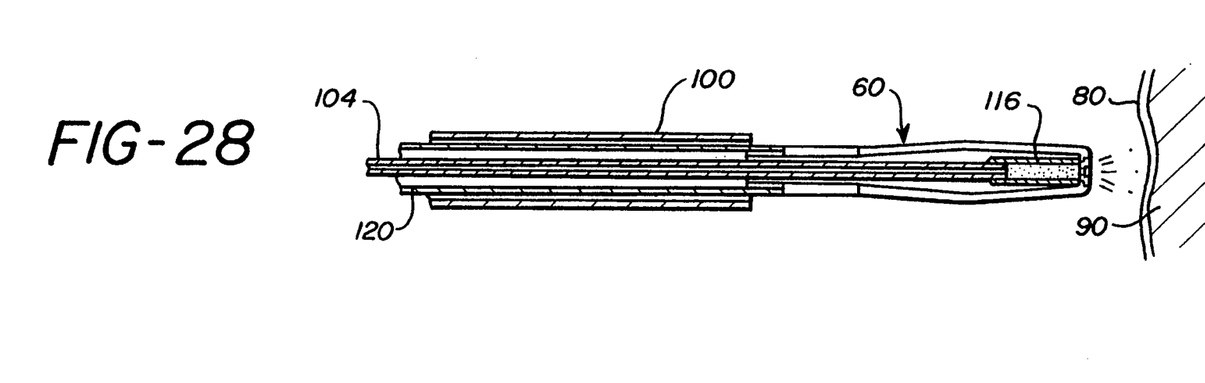

Next, as shown in FIG. 25, the deployment tube 102 and irrigation tube 104 are advanced relative to the delivery tube 100 to expose the operating tip 60 with the adhesion barrier 80 captured between the operating tip 60 and the tissue application area 90. Then, the deployment 102 is advanced, while the irrigation tube 104 remains stationary, to expand the operating tip 60 and form the flexible arms 62 into the desired shape to spread the adhesion barrier over the tissue application area 90. The operating tip 60 can be expanded into its convex shape (FIG. 26) to apply the adhesion barrier to a relatively flat application area, or into its concave shape (FIG. 27) to apply the adhesion barrier 80 to a curved tissue surface such as the outer surface of the ovaries. A saline solution can be applied via the irrigation tube 104 and the spray nozzle 116 to attach the adhesion barrier 80 in place on the tissue application area. Then, the operating tip is collapsed, as shown in FIG. 28, by retracting the deployment tube 102 relative to the irrigation tube 104. The operating tip 60 is used to tamp down the adhesion barrier 80 while a saline spray is supplied until the full surface of the adhesion barrier 80 is wet. After the adhesion barrier 80 is set in place, the operating tip 60 is retracted into the delivery tube 100 by retracting the deployment tube 102 and the irrigation tube 104 into the delivery tube 100. Finally, the adhesion barrier applicator 50 is withdrawn from the body through the incision.

The invention in its broader aspects is not limited to the specific details of the preferred embodiments shown and described, and those skilled in the art will recognize that the invention can be practiced with modification within the spirit and scope of the appended claims.

We claim:

1. An applicator for applying a sheet of surgical material to tissue, comprising:
    a delivery tube;
    a deployment tube slidably received within said delivery tube;
    a shaft slidably received within said deployment tube;
    an operating tip mounted at the distal end of said shaft and connected to the distal end of said deployment tube for engaging the sheet of surgical material, said operating tip being expandable by movement of said shaft relative to said deployment tube to apply the sheet of surgical material to the tissue; and actuator means for advancing said deployment tube and said shaft together relative to said delivery tube until said spreader tip is exposed at the distal end of said delivery tube and for advancing said deployment tube relative to said shaft when said spreader tip is exposed to expand said spreader tip to apply the sheet of surgical material to the tissue.

2. The applicator of claim 1, wherein:
said operating tip includes a plurality of flexible arms extending from the distal end of said shaft to the distal end of said tube, said arms being flexed outwardly when said tube is displaced relative to said shaft to spread the sheet of surgical material onto the tissue.

3. The applicator of claim 2, wherein:
each of said flexible arms has an intermediate portion which bulges radially outward when said arm is flexed for spreading the sheet of surgical material onto the tissue.

4. The applicator of claim 2, wherein:
said arms are spaced circumferentially apart about said operating tip.

5. The applicator of claim 2, wherein:
said arms are adapted to flex laterally outward into a convex shape to spread the sheet of surgical material over the tissue.

6. The applicator of claim 2, wherein:
said arms are adapted to flex into a concave shape at the distal end of said operating tip to spread the sheet of surgical material over the tissue.

7. The applicator claim 1, wherein:
said shaft comprises an irrigation tube for supplying fluid to the sheet of surgical material.

8. The applicator of claim 7, which includes:
a nozzle at the distal end of said irrigation tube for discharging the fluid therefrom.

9. An applicator for applying a spreadable sheet of surgical material to internal body tissue, comprising:
a delivery tube;
a deployment tube slidably received within said delivery tube;
a shaft slidably received within said deployment tube;
an expandable spreader tip mounted at the distal end of said shaft and connected to the distal end of said deployment tube for engaging the sheet of surgical material;
actuator means for advancing said deployment tube and said shaft together relative to said delivery tube to expose said spreader tip at the distal end of said delivery tube and for advancing said deployment tube relative to said shaft when said spreader tip is exposed to expand said spreader tip to spread the sheet of surgical material over the tissue; and
means for stopping the advancement of said shaft relative to said delivery tube with said spreader tip exposed, said spreader tip being expanded as said deployment tube is advanced relative to said shaft when said spreader tip is exposed.

10. The applicator of claim 9, wherein:
said spreader tip includes a plurality of flexible arms extending from the distal end of said shaft to the distal end of said deployment tube, said arms being flexed outwardly when said deployment tube is advanced relative to said shaft to spread the sheet of surgical material onto the tissue.

11. The applicator of claim 10, wherein:
each of said flexible arms has an intermediate portion which bulges radially outward when said arm is flexed for spreading the sheet of surgical material onto the tissue.

12. The applicator of claim 10, which includes:
said arms are spaced circumferentially apart about said spreader tip.

13. The applicator of claim 10, wherein:
said arms are flexible into a convex shape to spread the sheet of surgical material over the tissue.

14. The applicator of claim 10, wherein:
said arms are flexible into a concave shape to spread the sheet of surgical material over the tissue.

15. The applicator claim 9, wherein:
said shaft comprises an irrigation tube for supplying fluid to the sheet of surgical material.

16. The applicator of claim 15, which includes:
a nozzle at the distal end of said irrigation tube for discharging the fluid therefrom.

17. The applicator of claim 9, which includes:
means for releaseably holding said deployment tube in said delivery tube to retain said spreader tip retracted inside said delivery tube prior to the exposure of said spreader tip therefrom.

18. The applicator of claim 17, wherein:
said sheet of surgical material is draped over said spreader tip and held in said delivery tube prior to the exposure of said spreader tip therefrom.

19. The applicator of claim 9, which includes:
a funnel-shaped flange at the proximal end of said delivery tube for inserting said spreader tip and the sheet of surgical material into said delivery tube.

20. An endoscopic applicator for insertion into an endoscopic tube for applying an adhesion barrier to internal body tissue, comprising:
a delivery tube sized for insertion into the endoscopic tube;
a deployment tube slidably received within said delivery tube;
a shaft slidably received within said deployment tube;
an expandable spreader tip mounted at the distal end of said shaft and connected to the distal end of said deployment tube for engaging the adhesion barrier, said spreader tip assuming a collapsed configuration upon insertion into said delivery tube with said adhesion barrier;
actuator means for advancing said deployment tube and said shaft together relative to said delivery tube to expose said spreader tip and said adhesion barrier at the distal end of said delivery tube and for advancing said deployment tube relative to said shaft when said spreader tip is exposed to expand said spreader tip to apply the adhesion barrier to the tissue; and
means for stopping the advancement of said shaft relative to said delivery tube with said spreader tip and said adhesion barrier exposed, said spreader tip being expanded as said deployment tube is advanced relative to said shaft while said shaft remains stationary relative to said delivery tube.

21. The applicator of claim 20, wherein:
said spreader tip includes a plurality of flexible arms extending from the distal end of said shaft to the distal end of said deployment tube, said arms being flexed outwardly when said deployment tube is advanced relative to said shaft to spread the adhesion barrier onto the tissue.

22. The applicator of claim 21, wherein:
each of said flexible arms has an intermediate portion which bulges radially outward when said arm is flexed for spreading the adhesion barrier onto the tissue.

23. The applicator of claim 21, which includes:
said arms are spaced circumferentially apart about said spreader tip.

24. The applicator of claim 21, wherein:
said arms are flexible into a convex shape to spread the adhesion barrier over the tissue.

25. The applicator of claim 21, wherein:
said arms are flexible into a concave shape to spread the adhesion barrier over the tissue.

26. The applicator claim 20, wherein:
said shaft comprises an irrigation tube for supplying fluid to the adhesion barrier.

27. The applicator of claim 26, which includes:
a nozzle at the distal end of said irrigation tube for discharging the fluid therefrom.

28. The applicator of claim 26, which includes:
means for connecting said irrigation tube to an external source of fluid.

29. The applicator of claim 26, which includes:
a handle; and
a reservoir mounted on said handle for supplying fluid to said irrigation tube.

30. The applicator of claim 29, wherein:
said reservoir is slidably mounted on said handle for movement with said irrigation tube.

31. The applicator of claim 30, which includes:
a pump slidably mounted on said handle for movement with said reservoir for pumping fluid from said reservoir to said irrigation tube.

32. The applicator of claim 20, which includes:
means for releaseably holding said deployment tube in said delivery tube to retain said spreader tip retracted inside said delivery tube prior to the exposure of said spreader tip therefrom.

33. The applicator of claim 20, which includes:
a funnel-shaped flange at the proximal end of said delivery tube for inserting said spreader tip and the adhesion barrier into said delivery tube.

34. In combination, a spreadable sheet of surgical fabric and an applicator for applying said fabric to internal body tissue, said applicator comprising:
a delivery tube for receiving said sheet of surgical fabric;
a deployment tube slidably received within said delivery tube;
a shaft slidably received within said deployment tube;
an expandable spreader tip mounted at the distal end of said shaft and connected to the distal end of said deployment tube for engaging said sheet of surgical fabric, said spreader tip assuming a collapsed configuration upon insertion into said delivery tube with the sheet of surgical fabric thereon;
actuator means for advancing said deployment tube and said shaft together relative to said delivery tube to expose said spreader tip and said sheet of surgical fabric at the distal end of said delivery tube and for advancing said deployment tube relative to said shaft when said spreader tip is exposed to expand said spreader tip to spread the sheet of surgical fabric over the tissue; and
means for stopping the advancement of said shaft relative to said delivery tube with said spreader tip and said sheet of surgical fabric exposed, said spreader tip being expanded as said deployment tube is advanced relative to said shaft while said shaft remains stationary relative to said delivery tube.

35. The combination of claim 34, wherein:
said sheet of surgical fabric is draped over said spreader tip and held in said delivery tube prior to the exposure of said spreader tip therefrom.

36. The combination of claim 34, wherein:
said sheet of surgical fabric is absorbable by the internal body tissue.

37. An applicator for applying a spreadable sheet of surgical material to internal body tissue, comprising:
a delivery tube;
a deployment tube slidably received within said delivery tube;
a shaft slidably received within said deployment tube, said shaft having a distal end projecting beyond the distal end of said deployment tube;
an expandable spreader tip mounted at the distal end of said shaft and connected to the distal end of said deployment tube for spreading the sheet of surgical material over the tissue, said spreader tip being collapsed when inserted in said delivery tube with the sheet of surgical material;
a funnel-shaped flange at the proximal end of said delivery tube for inserting said spreader tip and the sheet of surgical material into said delivery tube;
actuator means for advancing said deployment tube and said shaft together relative to said delivery tube to expose said spreader tip and the sheet of surgical material at the distal end of said delivery tube and for advancing said deployment tube relative to said shaft when said spreader tip is exposed to expand said spreader tip to spread the sheet of surgical material over the tissue;
latch means for latching said shaft to said delivery tube with said spreader tip exposed, said spreader tip being expanded as said deployment tube is advanced relative to said shaft while said shaft remains stationary relative to said delivery tube; and
detent means for retaining said spreader tip retracted inside said delivery tube prior to the exposure of said spreader tip from the distal end of said delivery tube.

38. The applicator of claim 37, wherein said actuator means comprises:
a first finger grip secured to the distal end of said delivery tube and a second finger grip secured to the distal end of said deployment tube whereby said deployment tube is advanced relative to said delivery tube when said first and second finger grips are squeezed together.

39. The applicator of claim 37, wherein:
said deployment tube is movable relative to said shaft with said shaft and delivery tube latched together to expand and collapse said spreader tip.

40. The applicator of claim 37, wherein said latch means comprises:
a latch arm pivotally mounted on delivery tube and a latch member on said shaft which is releaseably engageable by said latch arm to stop the movement of said shaft relative to said delivery tube and to permit the movement of said deployment tube relative to said shaft.

* * * * *